United States Patent [19]

Kessler

[11] Patent Number: 5,419,902

[45] Date of Patent: May 30, 1995

[54] METHOD FOR INACTIVATING PATHOGENS

[75] Inventor: Jack Kessler, Ashland, Mass.

[73] Assignee: Symbollon Corporation, Sudbury, Mass.

[21] Appl. No.: 92,605

[22] Filed: Jul. 16, 1993

[51] Int. Cl.⁶ .................. A61K 38/44; C12N 11/00
[52] U.S. Cl. ........................ 424/94.4; 435/288; 435/262; 435/174; 435/176; 435/182
[58] Field of Search ............ 424/94.4; 435/288, 262, 435/174, 176, 182

[56] References Cited

U.S. PATENT DOCUMENTS

| | | | |
|---|---|---|---|
| 4,473,550 | 9/1984 | Rosenbaum et al. | 424/94 |
| 4,476,108 | 10/1984 | Kessler et al. | 424/50 |
| 4,588,586 | 5/1986 | Kessler et al. | 424/94.4 |
| 4,937,072 | 6/1990 | Kessler et al. | 424/94.4 |
| 4,996,146 | 2/1991 | Kessler | 435/28 |
| 5,043,176 | 8/1991 | Bycroft et al. | 426/332 |
| 5,227,161 | 7/1993 | Kessler | 424/94.4 |

Primary Examiner—David M. Naff
Assistant Examiner—Jean C. Witz
Attorney, Agent, or Firm—E. Lieberstein

[57] ABSTRACT

This invention relates to a method for inactivating pathogens using the peroxidase enzyme. The peroxidase enzyme is reacted with hydrogen peroxide or a source of hydrogen peroxide and an iodide anion to generate reaction products which are separated from the peroxidase enzyme and then used to inactivate pathogenic organisms.

12 Claims, No Drawings ically less than the corresponding specific activity in solution due to a number of factors not the least of which is diffusional constraints on substrates.

METHOD FOR INACTIVATING PATHOGENS

BACKGROUND OF THE INVENTION

A chemical system which uses the enzyme peroxidase, donor molecules and peroxide in an aqueous environment is taught in U.S. Pat. Nos. 4,476,108; 4,473,550; and 4,588,586. When the donor molecule is iodide peroxidase will catalyze the reduction of hydrogen peroxide to water with the concomitant oxidation of iodide anions. This system enzymatically generates an aqueous environment with reaction products and reaction by-products that inactivate pathogenic organisms. The solution generated with this chemistry contains; (1) the enzyme generated actives, (2) iodide at levels that are reduced from the initial concentration, (3) peroxide at levels that are reduced from the initial concentration, and (4) the protein peroxidase at the initial use concentration.

Peroxidases can be isolated from a variety of sources and their properties vary as a function of the source. The molecular weight of peroxidases ranges from 12,000 daltons for NADH peroxidase to 149,000 daltons for mycloperoxidase. The peroxidase as taught in U.S. Pat. Nos. 4,476,108; 4,473,550; and 4,588,586 is a peroxidase which falls under the Enzyme Commission's (E.C.) classification of 1.11.1.7. Practical considerations of cost and stability favor horseradish peroxidase as the preferred peroxidase within the E.C.I. 1.11.1.7 classification. Horseradish peroxidase has a molecular weight of about 40,000 daltons.

Peroxidases, with a few exceptions such as mycloperoxidase and cytochrome c peroxidase, are glycoproteins. Glycoproteins with a molecular weight greater than 10,000 daltons are known to act as immunogens in animals. Horseradish peroxidase is known to be an effective immunogen and it is possible to purchase antibodies to this protein commercially. In fact peroxidase-anti-peroxidase soluble complexes are sold as a reagent and used in (1) immunohistological applications on frozen or paraffin embedded tissue sections, (2) electron microscopy and (3) immunoblots. Both polyclonal and monoclonal antibodies are available to horseradish peroxidase.

Repeated contact of peroxidase with a wound or tissue could cause the formation of antiperoxidase antibodies. Once anti-peroxidase antibodies are formed within an animal, subsequent exposure to peroxidase could cause an allergic reaction. Such an allergic reaction can take the full spectrum of immediate and delayed types of allergic reactions produced by foreign macmomolecules. These reactions include exfoliative dermatitis, urticaria and angiodema, fever, asthma and even anaphylaxis.

It is obvious that a disinfectant that comes into contact, whether directly or indirectly, with animal or human wounds, tissues or organs should not contain immunogenic proteins. Therefore, peroxidase immunogenicity argues against such a use for the formulations described in the above mentioned patents. This application describes a method to form the active chemistry described in U.S. Pat. Nos. 4,476,108; 4,473,550; and 4,588,586 while minimizing or eliminating the potential for allergic reactions in animals and humans. The methods described in this application are effective against bacteria, fungi, spores and viruses.

SUMMARY OF THE INVENTION

A fundamental aspect of this invention is to use a peroxidase enzyme to form reaction products in the presence of substrates consisting of an aqueous source of hydrogen peroxide and an iodide; unreacted substrates and reaction products are then isolated, preferably be a separation process, from the peroxidase enzyme to form an independent source of biocidal agents for inactivating pathogens. In accordance with the present invention, the enzyme peroxidase is first immobilized to a solid support before it is reacted with the aqueous peroxide and iodide source to generate the reaction products which are then isolated apart from the peroxidase by a separation process. For purposes of the present invention the amount of oxidation of the iodide anions defines the reaction products.

Broadly, the present invention is a method for inactivating pathogens comprising the steps of:

immobilizing a peroxidase enzyme to a solid support;

contacting the immobilized peroxidase enzyme with a source of hydrogen peroxide and an iodide in an aqueous medium for forming a reaction product from the oxidation of iodide anions;

isolating said reaction products from the peroxidase enzyme to function as biocidal agents independent of said peroxidase enzyme; and contacting said pathogenic organisms with said reaction products.

Alternatively, it is possible to place non-immobilized peroxidase enzyme in dialysis tubing and diffuse a source of hydrogen peroxide and an iodide in an aqueous medium across the dialysis tubing to the enzyme for the purpose of forming a reaction product from the oxidation of iodide actions whereupon said reaction product would diffuse back across the dialysis tubing and thereby be separated from the non-immobilized peroxidase. This method is feasible does not offer the flexibility and process control inherent in the use of an immobilized enzyme.

A fundamental aspect of this invention is the physical separation of peroxidase from its reaction products prior to applying the peroxidase reaction products to surfaces for inactivation of pathogenic organisms. This invention describes the use of immobilized enzymes to achieve this separation. Enzymes and proteins may be immobilized to solid supports by different means. One method is to establish a covalent bond between the protein and a solid support. Another method is to covalently link agents to the solid support that tightly bind the protein of interest; by this expedient, the protein of interest is tightly bound when it contacts the linking agent. Once coupled to a solid support, enzymes are able to catalyze reactions when their substrates are brought into contact with said immobilized proteins. The rate of catalysis or specific activity for immobilized enzymes is typically less than the corresponding specific activity in solution due to a number of factors not the least of which is diffusional constraints on substrates.

A wide range of solid supports have been used to immobilize enzymes including porous glass, paper, wool, gold, silver, magnetic particles, latex, agarose, poly(hydroxymethacrylate), polyacrylamide and other porous polymers. Typically the solid support is first modified ("activated") with a chemical agent such that the solid support contains a functional group that can form a chemical bond to specific functional groups of proteins. Cyanogen bromide was one of the first activating agents used with agarose supports to immobilize proteins. Today there is a wide range of functional group chemistry that can be used to link proteins to solid supports for immobilizing enzymes. These chemical groups include epoxyl derivitives, maleimides, oxiranes, hydrazides, p-nitrophenyl chloroformate and other haloacetyl derivatives, divinyl sulfones, epichlorohydrin and succinimidyl esters including N-hydroxysuccinimide.

A column is the most common physical format for use of an immobilized enzyme. In column processing a liquid containing the enzyme's substrates is passed through a packed column that contains the immobilized enzyme. The flow rate of the liquid is closely controlled and pumped into an inlet port that lies at one end of the column. The products of the reaction are collected from the column at the outlet port on the opposite side of the column. Alternatively the products can be pumped back over the immobilized enzyme column. Another physical format that is used with immobilized enzymes is batch processing. Batch processing is performed by suspending the solid matrix in a solution that contains the reaction substrates and then removing the solid matrix by a physical technique such as filtration after the reaction has reached its desired stage of completion.

In accordance with the present invention the immobilized peroxidase generates a biocidal composition that is subsequently separated from the immobilized enzyme to yield biocidal agents which do not contain a peroxidase enzyme. It has been observed that immobilized peroxidase can catalyze the reaction between peroxide and iodide when they are brought into contact in an aqueous environment and effect the oxidation of substantial amounts of the initial concentration of iodide. In addition, the biocidal properties of the reaction products are maintained once the reaction products are removed from the immobilized enzyme for a period of time sufficient for the inactivation of pathogenic organisms or surfaces distinct and distant from those in which the peroxidase reaction was originated.

The peroxidase of this invention is identified by the International Union of Biochemistry and the International Union of Pure and Applied Chemistry by the Enzyme Commission identification number E.C. 1.11.1.7. Peroxidase can be obtained from a wide variety of sources. The least expensive and most robust peroxidase suitable for this application is horseradish peroxidase although lactoperoxidase can also be used. Commercially obtained peroxidase comes lyophilized as a dry powder and must be attached to a solid support prior to use. There are no limitations on the material composition which is suitable for use as a solid support for peroxidase. It is possible to purchase preactivated solid supports that can be mixed with peroxidase under defined conditions to generate the immobilized enzyme.

Activated solid supports are available from a variety of commercial sources. These materials are usually composed of a porous polymeric backbone that is derivitized with functional groups that react with amino, carboxyl, sulfhydral or arginyl groups on proteins. It is preferable to select a solid phase material that has a large surface area to maximize binding of protein to the solid support. In addition a preferred solid phase will permit a rapid flow rate when packed into a column. Examples of preferred solid phase materials for the immobilization of peroxidase include carboxylated latex particles, controlled pore glass, aminoethyl polyacrylamide gels, adipic acid dihydrazide agarose, amino-benzyloxymethylcellulose, bromoacetyl-cellulose, and N-hydroxysuccinimide agarose.

The donor molecule of this invention is iodide anion which serves as a substrate for the enzyme peroxidase. Suitable sources of iodide anion for this invention include sodium iodide and potassium iodide as well as other salts of iodide. The simple salts of iodide have the advantage of being relatively inexpensive. Iodide anion must be dissolved in an aqueous environment and contacted with the immobilized enzyme in the presence of hydrogen peroxide. It is suitable to use a buffer which contains iodide anion to equilibrate the solution in which the immobilized enzyme is equilibrated prior to initiation of the reaction. The range of iodide anion used for this invention ranges between 0.15–5.0 mg/mL. The preferred range for iodide anion lies between 0.5 and 2.0 mg/mL and is a function of the pH, ionic strength and the peroxide concentration.

Hydrogen or methyl peroxide is the oxidant that acts as a substrate for this reaction. Peroxide is a less stable molecule than iodide in solution and it is preferable to add the peroxide as the last component in this reaction. The concentration range of peroxide suitable for this invention lies between 0.005 and 01.50% (w/w). The preferred range of peroxide will vary with the pH of the aqueous environment and the concentration of iodide but typically lies between 0.01–0.2%. Suitable materials which can serve as precursors for hydrogen peroxide include metal peroxides, percarbonates, persulphates, perphosphates, peroxyesters, urea peroxide, peroxyacids, alkylperoxides, acylperoxides and perborates. Mixtures of two or more of these substances can also be used. Sodium percarbonate is particularly suitable because it is delivers approximately 29% (w/w) hydrogen peroxide once it is dissolved in water and it is composed of chemical that are generally regarded as safe.

At least 25% of the initial concentration of iodide anions should be oxidized to yield reaction products that have an acceptable level of biocidal activity. The preferred range of oxidation for the iodide anions is 75–95% of the initial concentration of iodide anions. There is no requirement on the percentage of hydrogen peroxide that must be reduced to water in order to yield reaction products that have an acceptable level of biocidal activity. However, on a mole to mole basis, the amount of hydrogen peroxide that must be enzymatically reduced is equal to at least 12.5% of the initial molar concentration of iodide anions. The preferred amount of hydrogen peroxide that should be reduced is equal to 40–200% of the initial concentration of iodide anions.

Suitable buffers for this invention include phosphate, citrate, carbonate and Goode buffers. Any buffer which has the capacity to control the pH to within ±0.10 pH units operating under a constant temperature between 6° and 55° C. is suitable for use with this invention.

Immobilized enzyme preparations can be used in a column format or in a batch process. For batch operations the reaction should be allowed to run with mixing until the reaction has reached an equilibrium. The equilibrium point is that point in the reaction at which the concentration of iodide anton does not change in concentration more than 1.0% per hour. For column operations the effluent from the column can be pumped back onto the column until the column effluent has reached equilibrium as described above. Alternatively, the flow rate through the column can be adjusted until the reaction has reached its equilibrium concentration.

The concentration of iodide anion, peroxide, pH and reaction time will determine the amount of oxidation of iodide anions (i.e., reaction products). Once the reaction is initiated the concentration of iodide anions will decrease as they are oxidized. Reaction conditions should be controlled so that the concentration of iodide anion decreases by at least 25% and may be decreased by as much as 95%. The level of iodide oxidation will vary with pH and the concentration of peroxide. The preferred range for iodide oxidation is between 75-95%. Reaction conditions must be controlled so that the concentration of hydrogen peroxide decreases by an amount that is equal to at least 12.5% of the initial concentration of iodide anions. The preferred range for peroxide reduction is equal to an amount that is equal to at least 40% of the initial concentration of iodide anions.

The reaction product is easily separated from the immobilized enzyme by such simple methods as filtration or magnetic separation. Once the reaction product is separated from the immobilized enzyme it can be directly applied animal or human tissue including ocular tissue. Applications of the reaction products to mammalian tissues include use as a lavage during invasive surgery, as a wound disinfectant, as a whole body disinfectant or as a disinfectant for burns. Alternatively, the reaction product can be applied to solid surfaces such as metals, plastics, minerals, natural and synthetic fibers and paper or polymeric membranes. The application of the separated reaction product to inanimate or living tissue is easily accomplished by simply transferring the fluid by a suitable vessel and then depositing the reaction product onto the desired surface.

EXAMPLES

Example 1

Cyanogen bromide (Sigma Chemical Co. Cat. No. C-1150) and 1-1' carbonyldimidazole (Sigma Chemical Co. Cat. No. C-8778) activated agarose gels were coupled to horseradish peroxidase. The amount of immobilized enzyme coupled to these gels was estimated by quantifying the total absorbance at 280 and 405 nm prior to and after the coupling reaction. The amount of enzymatic activity prior to and after enzyme immobilization to these gels was determined using the precipitating substrate 1-1'chloro-4naphthol (Sigma Chemical Co. Cat. No. C-6788).

One gram of cyanogen bromide activated gel was swollen in 10 mL of 10 millimolar sodium phosphate buffer, pH 6.0. Five mL of the 1-1' carbonyldiamidazole activated gel and 10 mL of the swollen cyanogen bromide activated gel were each added to a separate 15 mL centrifuge tube and spun down at 1,500 rpm for 5 minutes in a centrifuge. The supernatant was poured off and 10 mL of phosphate buffer was added. The gels were mixed for at least 20 seconds beyond the time that they appeared fully suspended. A 5 mL aliquot of the reconstituted gel suspension was added to a new centrifuge tube. A 5 mL aliquot of the phosphate buffer was added to each tube that contained the gels and spun down in the centrifuge. The supernatant was poured off, and the gels were resuspended in 10 mL of phosphate buffer. This procedure of suspension, centrifugation, and supernatant removal was repeated five more times for each gel. Upon completion of the fifth washing, the supernatant was poured off gently and each gel was resuspended to a total volume of 5 mL using 10 millimolar phosphate buffer at a pH of 6.0. The gels were stored in the refrigerator overnight.

TABLE I

Total Absorbence Units Applied and Recovered from Gels

| Supernatant | Volume | Abs. 405 | Abs 280 | Total 405 | Total 280 |
| --- | --- | --- | --- | --- | --- |
| CB-gel | 8.0 mL | .2124 | .2566 | 17.0 | 20.5 |
| CI-gel | 8.3 mL | .2145 | .2471 | 17.8 | 20.5 |
| Enzyme Stock | 5.0 mL | .4808 | .6938 | 24.0 | 34.7 |

A stock solution of class II horse radish peroxidase (HRP) from Biozyme Laboratories (San Diego, Calif.) was prepared at a concentration of 10 mg/mL. A 5 mL aliquot of the HRP stock solution was added at 8° C. to (A) 5 mL of the cyanogen bromide activated gel (CB-gel) and (B) 5 mL of the 1-1' carbonyldimidazole activated gel (CI-gel) and the solutions were gently mixed at 8° C. for 10 hours. The gels were centrifuged for 10 minutes at 1,500 rpm. Each supernatant was collected separately. Each supernatant and the enzyme stock solution was diluted tenfold in water and their absorbances were measured at 280 and 405 nm. The results of these measurements are above in Table I.

The absorbance results indicate that an upper limit of about 40% of the applied protein was coupled to the gel. This is calculated by determining the ratio of recovered protein to the applied protein as determined by absorbance measurements. This indicates that about 20 mg of HRP was bound to each type of gel. The amount of enzymatic activity expressed by the immobilized enzyme as compared to the total amount of enzymatic activity applied to the gels was determined and the results are shown in Table II.

TABLE II

Total Applied and Immobilized Relative Peroxidase Activity Units

| Sample | Volume | Time (sec) | Dilution | Total Units |
| --- | --- | --- | --- | --- |
| CB-gel | 5.0 mL | 30 | 1/1,000 | 166 |
| CI-gel | 5.0 mL | 51 | 1/1,000 | 98 |
| Applied HRP | 5.0 mL | 28 | 1/10,000 | 1,780 |

A unit of enzyme activity was determined by measuring the amount of time required to form a visually detectable precipitate at 25° C. using 200 μl of the substrate 1-1' chloro-4-naphthol (Sigma Chemical Co. Cat. No. C-6788) and 10 μl of sample. The amount of total relative enzyme units was calculated by multiplying the sample dilution times the sample volume and dividing by the time required to observe a precipitate. The uncoupled HRP that was applied to the gel had a relative "specific activity" of 35.6 units per mg. Immobilized enzyme exhibited a relative specific activity of 5.62 and 3.31 units per mg for CB-gel and CI-gel respectively. These activity measurements are useful in that they allow for a comparison between the different forms of the enzyme; there is no significance to these measurements this fact.

The immobilized enzyme was physically separated from the buffer in which it was stored in order to determine if any of the enzyme activity was "uncoupled" i.e., associated with the buffer and not the solid matrix. The estimate of uncoupled peroxidase activity in the immobilized enzyme samples was determined by centrifuging a sample of immobilized enzyme and measuring the peroxidase activity in 10 μl of the supernatant. Undiluted supernatant of CI-gels and CB-gels did not develop a precipitate after incubation for two hours at 25° C. This means that the amount of uncoupled or soluble peroxidase activity in the gels is less than 0.04% of the activity attributed to immobilized enzyme.

Example 2

Horseradish peroxidase was dissolved at a concentration of 20 mg/mL in 0.10 molar sodium acetate buffer at pH 5.0 and stored in a refrigerator. Ten mL of the peroxidase solution was mixed with 5 mL of Aft-Gel 10 (Bio-Rad Laboratories, Hercules, Calif.; catalog number 153-6046). The gel slurry was mixed at 4° C. for 4 hours and then the coupling reaction was stopped by pouring the gel suspension into a 1.5×10 cm column with a 35 micron porous support disc. The gel rests on the support disc and the reaction fluid was allowed to drain by gravity. Water was immediately added to the column before the solid support dried. One hundred mL of a 0.010 molar ethanolamine -hydrochloric acid mixture at a pH of 8.0 was run through the gel under gravity. One hundred mL of a 0.50 molar sodium phosphate buffer at a pH of 7.5 was run over the column under gravity. Three sequential 100 mL volumes of a pH 7.5 phosphate buffer mixture was run over the column; the molarities of the phosphate buffers were 0.3, 0.20 and 0.10 molar. Finally the gel was stored in 10 mL of a 0.10 molar sodium phosphate buffer at a pH of 5.0.

A reaction between the immobilized peroxidase, iodide anions and peroxide was initiated as follows. The immobilized enzyme slurry was diluted in water to a concentration where its activity was 0.05 relative units per mL. The activity per mL of the immobilized enzyme was measured relative to the activity of soluble peroxidase by measuring the time required to develop a visually perceptible precipitate with the substrate 4-chloro-1-napthol (Sigma Chemical Co., St. Louis, Mo.; catalog number C-6788). One mL of immobilized enzyme slurry in water was added to 8 mL of a 1.25 mg/mL stock solution of sodium iodide in 20 millimolar citrate-phosphate buffer, pH 5.0. One mL of a 0.5 % hydrogen peroxide solution was added to this mixture and the resulting suspension was mixed using a small magnetic stir bar at 20° C. for 1 hour.

The reaction product was separated from the immobilized enzyme and used to inactivate pathogenic organisms. After 1 hour the suspension was filtered through a disk filter into a glass vial. The glass vial was sealed and stored at room temperature. One minute after filtration, a 0.75 mL aliquot of the reaction product was withdrawn from the vial and added to a test tube which contained 0.1 mL of a suspension of Staphlococcus aureus in normal saline at a concentration of $10^7$ colony forming units (cfu) per mL. The components were mixed and incubated at 25° C. for 10 minutes. A 0.5 mL aliquot was withdrawn from the sample and added to 25 mL of typticase soy both (TSB) that contained 0.25% sodium thiosulfate as neutralizer. TSB has a final pH of 7.3 and is comprised of 17 grams pancreatic digest of casein; 3 grams papaic digest of soy meal; 5 grams sodium chloride; 2.5 grams glucose; 2.5 grams potassium phosphate dibasic; 1000 ml of distilled water. This mixture was incubated at 37° C. for three days and examined for signs of growth.

Samples of the immobilized enzyme reaction product were withdrawn and tested as described above at 1, 15, 30, 45, 60, 90, 120, and 180 minutes. A viability control was run in which water was substituted for the reaction product of the immobilized enzyme. The results of this experiment are shown in Table III.

TABLE III

| Inactivation of Staphlococcus aureus Treated with Immobilized Peroxidase Reaction Products | | | | | | | | |
|---|---|---|---|---|---|---|---|---|
| Time (min.) | control | 1 | 15 | 30 | 45 | 60 | 90 | 120 | 180 |
| Growth | yes | no | no | no | no | no | no | no | no |

Example 3

Horseradish peroxidase was dissolved at a concentration of 40 mg/mL in water. Ten mL of the peroxidase solution was mixed with 10 mL of Affi-Gel 102 (Bio-Rad Laboratories, Hercules, California; catalog number 153-2401) and diluted with 10 mL of 20 millimolar sodium phosphate at pH 6.0. The gel slurry and enzyme solution was mixed on a rocker arm at 4° C. for 30 minutes to allow for temperature equilibration. The two solutions were combined and the pH was adjusted to 5.0 with 1 normal hydrochloric acid (HCl). Fifty milligrams of 1-ethyl-3(3-dimethylaminopropyl) carbodiimide hydrochloride was added to the solution and the pH was immediately adjusted to 5.0 with 1.0 normal HCl. The reaction was mixed on a rocker arm at 4° C. for 24 hours.

The coupling reaction was stopped by pouring the gel suspension into a 2.5×10 cm column with a 35 micron porous support disc. The gel rests on the support disc and the reaction fluid was allowed to drain by gravity. Water was immediately added to the column before the solid support dried. One hundred mL of a 0.50 molar citrate-phosphate buffer at a pH of 5.0 was run over the column under gravity. Three sequential 100 mL volumes of a pH 5.0 citrate-phosphate buffer mixture was then run over the column; the molarities of the phosphate buffers were 0.3, 0.20 and 0.10 respectively. Finally the gel was stored in 20 mL of a 0.10 molar citrate-phosphate buffer at a pH of 5.0.

A reaction between the immobilized peroxidase, iodide anions and peroxide was initiated as follows. The immobilized enzyme slurry was diluted in water to a concentration where its activity was 0.05 units per mL as described above. One mL of immobilized enzyme slurry in water was added to 8 mL of a 5.0 mg/mL stock solution of sodium iodide in 20 millimolar citrate-phosphate buffer, pH 5.0. One mL of a 0.1% hydrogen peroxide solution was added to this mixture and the resulting suspension was mixed using a small magnetic stir bar at 20° C. for 2 hours. The reaction product was separated from the immobilized enzyme and used to inactivate pathogenic organisms.

After 2 hours the suspension was filtered through a disk filter into a glass vial. The glass vial was sealed and stored at room temperature. Five minutes after filtration, a 0.50 mL aliquot of the reaction product was withdrawn from the vial and added to a test tube which contained 0.050 mL of a suspension of E. coli in normal saline at a concentration of $10^7$ cfu per mL. The components were mixed and incubated at 25° C. for 10 minutes. A 0.25 mL aliquot was withdrawn from the sample and added to 25 mL of TSB as described above in Example 2.

Samples of the immobilized enzyme reaction product were withdrawn and tested as described above at 30, 60, 90, 120, and 180 minutes. A viability control was run in which water was substituted for the reaction product of the immobilized enzyme. The viability control was only sampled at 10 minutes. The results of this experiment are shown in Table IV.

TABLE IV

Inactivation of *E. coli* Treated with Immobilized Peroxidase Reaction Products

| Time (min.) | control | 10 | 30 | 60 | 90 | 120 | 180 |
|---|---|---|---|---|---|---|---|
| Growth | yes | no | no | no | no | no | no |

Example 4

A ten mL aliquot of a 2.5% (w/w) suspension of carboxylated latex particles (Sigma Chemical Co. Chemical Company, St. Louis, Mo.; catalog number CLB-4) was placed in a 50 mL screw top plastic vial and centrifuged for 5 minutes at 2,500 revolutions per minute (rpm) in a centrifuge (Centra-7R, International Equipment Company). The supernatant was poured off and the particles were resuspended by mechanical nutation in 40 mL of 10 millimolar sodium borate, pH 8.5. These steps serve to wash the beads. The wash procedure was repeated a total of three times and the final suspension was made in 0.10 molar sodium phosphate at pH 7.5. The wash procedure was repeated four more times using 0.10 molar sodium phosphate at pH 7.5 and the final suspension was prepared such the beads were 2.5% (w/v) in 0.10 molar sodium phosphate at pH 7.5.

A 2% solution of fleshly prepared carbodiimide was made and 15 mL of this solution was added to 12 mL of the 2.5% (w/v) carboxylated beads. This suspension was mixed at room temperature on a rocker and for 2 hours. The suspension was then centrifuged and the supernatant was poured off. The following sequence was repeated three times: the beads were suspended in 10 millimolar sodium borate, pH 8.5, mixed and the supernatant was poured off. The beads were then resuspended in 25 mL of 10 millimolar sodium borate, pH 8.5 and 4 mg of protein was added to the suspension. This suspension was mixed on a rocker arm at room temperature overnight. The next day the beads were centrifuged, washed three limes in 10 millimolar phosphate buffer, pH 7.0, suspended in 0.02 molar ethanolamine for 45 minutes, washed three times, suspended in 1.0% bovine serum albumin for 60 minutes, washed three times and then suspended in 10 millimolar sodium phosphate buffer at a pH of 6.0. The reaction product was separated from the immobilized enzyme and used to inactivate pathogenic organisms.

*Tricbopbyton mentagrophytes* (ATCC 9533) was stored at 2°–5° C. on agar slants at a pH of 6.2 ±0.1. The slants were composed of 2% glucose, 1% Neopeptone (Difco) and 2% agar. Petri dish cultures were prepared by planting innoculum at the center of an agar plate and incubating for 13 days at 25°–30° C. Mycelial mats were removed from the surface of 5 agar plate cultures and transferred to a sterilized glass tissue grinder. The mycelial mats were combined with 25 mL of sterile normal saline and homogenized. The resulting suspension was filtered through sterile absorbent cotton to remove hyphal elements. The density of this conidial suspension was estimated by counting in a hemocytometer and storing a stock suspension at a concentration of $1.5 \times 10^8$ conidia per mL at 6° C.

A reaction between the immobilized peroxidase, iodide anions and peroxide was initiated as follows. The immobilized enzyme slurry was washed in deionized water and then diluted in deionized water to a concentration where its activity was 0.005 units per mL as described in Example 1. One mL of immobilized enzyme slurry in water was added to 5 mL of a 4.0 mg/mL stock solution of sodium iodide in 20 millimolar citrate-phosphate buffer, pH 4.5. One mL of a 0.2% hydrogen peroxide solution was added to this mixture and the resulting suspension was mixed overnight at room temperature using a small magnetic stir bar in a sealed glass container. The reaction product was separated from the immobilized enzyme and used to inactivate pathogenic organisms.

After 19 hours the enzyme reaction was filtered through a disk filter into a glass vial. The glass vial was sealed and stored at room temperature. Thirty minutes after filtration, a 1.0 mL aliquot of the reaction product was withdrawn from the vial and added to a test tube which contained 0.050 mL of a suspension of *Trichophyton mentagrophytes* at a concentration of $1.5 \times 10^8$ conidia per mL as described above. The components were mixed and incubated at 25° C. A 0.25 mL aliquot was withdrawn from the sample, added to 0.25 mL of normal saline containing 0.1% sodium thiosulfate and spread on an agar plate. The agar plates were incubated for 13 days at 25°–30° C. to determine viability. In order to run positive controls, water was substituted for sodium iodide.

Control plates were overgrown with *T. mentagrophytes*. No growth was observed on any of the experimental plates. When the organism was exposed for 1 minute to the reaction products growth was observed in all cases.

Example 5

Horseradish peroxidase was dissolved at a concentration of 0.5 mg/mL in water that contained 1 mg/mL of albumin. Ten mL of the peroxidase solution was added into hydrated dialysis tubing (SpectraPor 4; Fisher Scientific) with a molecular weight cut-off 12,000 to 14,000 daltons. The dialysis tubing was tied and allowed to come to equilibrium for 30 minutes in a 125 mL beaker containing 100 mL of a 0.50 molar citrate-phosphate buffer at a pH of 5.0.

A reaction between the peroxidase trapped inside of the dialysis tubing was initiated as follows. Iodide anions and peroxide were added to the beaker so that their final concentration outside of the dialysis tubing was 2 mg/mL with respect to potassium iodide and 0.03% with respect to hydrogen peroxide. The solution was mixed using a small magnetic stir bar at 20° C. The reaction product was observed to diffuse away from the interior of the dialysis tubing into the larger dialysate. Sample of the reaction product were taken from the dialysate after two hours and used to inactivate pathogenic organisms.

A 1.0 mL aliquot of the reaction product was withdrawn from the vial and added to a test tube which contained 0.10 mL of a suspension of *E. coli* in normal saline at a concentration of $10^7$ cfu per mL. The components were mixed and incubated at 25° C. for 10 minutes. A 0.25 mL aliquot was withdrawn from the sample and added to 25 mL of TSB as described above in Example 2. This mixture was incubated at 37° C. for three days and examined for signs of growth. No growth was observed.

What I claim is:

1. A method for inactivating pathogens comprising the steps of:
    immobilizing a peroxidase enzyme within the classification E.C. 1.11.17 to a solid support;

contacting the immobilized peroxidase enzyme with a source of hydrogen peroxide and an iodide in an aqueous medium for forming reaction products from the oxidation of iodide anions such that the reaction products contain at least 25% of the initial concentration of iodide anions in an oxidized state and with said initial concentration of iodide anions in said aqueous source at the outset of forming the reaction products equal to at least 0.15mg/ml;

separating said reaction products from said immobilized peroxidase enzyme so that, said reaction products function as a biocidal agent independent of said peroxidase enzyme; and contacting said pathogenic organisms with said separated reaction products after a time duration of at least one minute.

2. A method as defined in claim 1 wherein said peroxidase enzyme is immobilized to a solid support selected from the group consisting of activated latex particles, controlled pore glass, polyacrylamide gels, agarose gels, derivitized cellulose, activated magnetic particles, activated gold, activated paper and activated plastics.

3. A method as defined in claim 1 wherein said peroxidase is activated using a chemical agent selected from the group consisting of epoxyl derivatives, malemides, oxiranes, hydrazides, haloacetyl derivatives, divinyl sulfones, epichlorohydrin and succinimidyl esters.

4. A method as defined in claim 1 wherein said immobilized peroxidase enzyme is horseradish peroxidase.

5. A method as defined in claim 4 wherein said immobilized peroxidase enzyme contacts said aqueous peroxide source of hydrogen peroxide and iodide in a batch or column operation with the reaction continued until an equilibrium point is reached at which time the concentration of iodide anion does not change in concentration more than 0.1% per hour.

6. A method as defined in claim 4 wherein said immobilized enzyme contacts said aqueous source of hydrogen peroxide and iodide in an immobilized enzyme column.

7. A method as defined in claim 4 wherein the concentration of peroxide lies in a range between 0.005 and 3.0% with a preferred range for hydrogen peroxide between 0.05–1.5%.

8. A method as defined in claim 4 wherein the concentration of iodide anion lies between 0.15–5.0 mg/mL with a preferred range for iodide anion between 1.0 and 2.5 mg/mL.

9. A method as defined in claim 8 wherein said aqueous source of hydrogen peroxide and iodide further comprises a buffering agent selected from the group consisting of phosphate, citrate, carbonate and Goode buffers.

10. A method as defined in claim 4 wherein said pathogenic organisms are found on animal or human tissue.

11. A method as defined in claim 4 wherein said pathogenic organisms are found on metals, plastics, minerals, natural fibers, synthetic fibers, paper or polymeric membranes.

12. A method of inactivating pathogens comprising the steps of:

placing a peroxidase enzyme on one side of a dialysis membrane;

placing a source of hydrogen peroxide and an iodide in an aqueous medium on the dialysate side of the dialysis tubing for a time sufficient to cause said peroxide and iodide to contact the peroxidase enzyme by means of diffusion through the dialysis tubing for forming reaction products from the oxidation of iodide anions such that the reaction products contain at least 25% of the initial concentration of iodide anions in an oxidized state with said initial concentration of iodide anions at the outset of forming the reaction products equal to at least 0.15 mg/ml;

separating said reaction products from said immobilized peroxidase enzyme by sampling the dialysate side of the dialysis tubing so that said reaction products function as biocidal agents independent of said peroxidase enzyme; and contacting said pathogenic organisms with said separated reaction products.

* * * * *